(12) United States Patent
Sakai

(10) Patent No.: US 10,456,032 B2
(45) Date of Patent: Oct. 29, 2019

(54) OPHTHALMIC IMAGING APPARATUS AND OPHTHALMIC IMAGE PROCESSING APPARATUS

(71) Applicant: TOPCON CORPORATION, Itabashi-ku, Tokyo (JP)

(72) Inventor: Jun Sakai, Kuki (JP)

(73) Assignee: TOPCON CORPORATION, Itabashi-ku, Tokyo (JP)

(*) Notice: Subject to any disclaimer, the term of this patent is extended or adjusted under 35 U.S.C. 154(b) by 0 days.

(21) Appl. No.: 15/680,349

(22) Filed: Aug. 18, 2017

(65) Prior Publication Data
US 2018/0070818 A1 Mar. 15, 2018

(30) Foreign Application Priority Data
Sep. 9, 2016 (JP) .................. 2016-176009

(51) Int. Cl.
| G06K 9/00 | (2006.01) |
|---|---|
| A61B 3/12 | (2006.01) |
| G06T 7/73 | (2017.01) |
| A61B 3/00 | (2006.01) |
| A61B 3/10 | (2006.01) |

(Continued)

(52) U.S. Cl.
CPC .......... *A61B 3/1233* (2013.01); *A61B 3/0025* (2013.01); *A61B 3/0041* (2013.01); *A61B 3/102* (2013.01); *G06T 5/008* (2013.01); *G06T 5/50* (2013.01); *G06T 7/0012* (2013.01); *G06T 7/13* (2017.01); *G06T 7/155* (2017.01); *G06T 7/187* (2017.01); *G06T 7/73* (2017.01); *A61B 3/13* (2013.01); *A61B 3/135* (2013.01); *G06T 2207/10101* (2013.01); *G06T 2207/20044* (2013.01); *G06T 2207/20192* (2013.01); *G06T 2207/30041* (2013.01); *G06T 2207/30104* (2013.01)

(58) Field of Classification Search
CPC combination set(s) only.
See application file for complete search history.

(56) References Cited

U.S. PATENT DOCUMENTS

| 2012/0184845 A1* | 7/2012 | Ishikawa ............... A61B 3/102 600/425 |
|---|---|---|
| 2013/0301008 A1 | 11/2013 | Srivastava et al. |

(Continued)

FOREIGN PATENT DOCUMENTS

| JP | 2013-184018 A | 9/2013 |
|---|---|---|
| JP | 2015-515894 A | 6/2015 |

*Primary Examiner* — Alex Kok S Liew
(74) *Attorney, Agent, or Firm* — Chiesa Shahinian & Giantomasi PC (57) ABSTRACT

An ophthalmic imaging apparatus of an embodiment includes a data acquisition unit, a blood vessel enhanced image forming unit, and a blood vessel gradient distribution determination unit. The data acquisition unit is configured to acquire a three dimensional data set of a fundus of a subject's eye using optical coherence tomography (OCT). The blood vessel enhanced image forming unit is configured to form a blood vessel enhanced image based on the three dimensional data set. The blood vessel gradient distribution determination unit is configured to determine a blood vessel gradient distribution that shows gradients of blood vessels at a plurality of locations in the fundus, based on the blood vessel enhanced image.

9 Claims, 7 Drawing Sheets

(51) Int. Cl.
*G06T 5/00* (2006.01)
*G06T 7/00* (2017.01)
*G06T 5/50* (2006.01)
*G06T 7/13* (2017.01)
*G06T 7/155* (2017.01)
*G06T 7/187* (2017.01)
*A61B 3/13* (2006.01)
*A61B 3/135* (2006.01)

(56) References Cited

U.S. PATENT DOCUMENTS

| | | | |
|---|---|---|---|
| 2014/0276025 A1* | 9/2014 | Durbin | A61B 5/4842 600/427 |
| 2015/0313466 A1 | 11/2015 | Yoshida et al. | |
| 2016/0302738 A1 | 10/2016 | Yoshida et al. | |
| 2016/0317029 A1 | 11/2016 | Srivastava et al. | |

* cited by examiner

OPHTHALMIC IMAGING APPARATUS AND OPHTHALMIC IMAGE PROCESSING APPARATUS

CROSS-REFERENCE TO RELATED APPLICATION

This application is based upon and claims the benefit of priority from Japanese Patent Application No. 2016-176009, filed Sep. 9, 2016; the entire contents of which are incorporated herein by reference.

BACKGROUND

Diagnostic imaging is important in ophthalmology. Optical coherence tomography (OCT) is utilized more and more in recent years. OCT is used not only for the acquisition of B mode images and three dimensional images but also for the acquisition of front images (or enface images) such as C mode images and shadowgrams.

In addition, there are diagnostic imaging technique for acquiring images in which a specific site of an eye is enhanced, and for acquiring functional information. For example, based on time-series volume data acquired with OCT, B mode images and front images in which retinal blood vessels and choroid blood vessels are enhanced can be constructed. Such images are referred to as blood vessel enhanced images, blood vessel high-contrast images, angiograms, or the like. Such imaging technique is referred to as OCT angiography or the like. Further, blood flow information can be determined based on phase information of data acquired with OCT. Such imaging technique is referred to as OCT blood flow measurement, or the like.

Conventional technology related to the above is disclosed, for example, in Japanese Unexamined Patent Application Publication (Translation of PCT Application) No. 2015-515894, and Japanese Unexamined Patent Application Publication No. 2013-184018.

BRIEF SUMMARY

An ophthalmic imaging apparatus of an embodiment includes: a data acquisition unit configured to acquire a three dimensional data set of a fundus of a subject's eye using optical coherence tomography (OCT); a blood vessel enhanced image forming unit configured to form a blood vessel enhanced image based on the three dimensional data set; and a blood vessel gradient distribution determination unit configured to determine a blood vessel gradient distribution that shows gradients of blood vessels at a plurality of locations in the fundus, based on the blood vessel enhanced image.

An ophthalmic image processing apparatus of an embodiment includes: a data reception unit configured to receive a three dimensional data set of a fundus of a subject's eye acquired using optical coherence tomography (OCT); a blood vessel enhanced image forming unit configured to form a blood vessel enhanced image based on the three dimensional data set; and a blood vessel gradient distribution determination unit configured to determine a blood vessel gradient distribution that shows gradients of blood vessels at a plurality of locations in the fundus, based on the blood vessel enhanced image.

DETAILED DESCRIPTION

Exemplary embodiments of the present invention will be described in detail with referring to the drawings. The contents of the documents cited in the present specification and any other known art may be applied to the embodiments below.

The embodiment is configured to apply OCT angiography to determine a blood vessel gradient distribution that is a distribution of gradient (i.e., angle, inclination angle, slope angle, slanting angle, or the like) of blood vessels of an eye fundus. The blood vessel gradient distribution can be used, for example, for diagnosis and other modalities. A typical example of such modalities is OCT blood flow measurement.

The gradient of a blood vessel may be defined with an arbitrary direction as a reference (i.e., the angle=0 degree). For example, the A (Axial) scan direction (i.e., the A line direction) of OCT can be used as the reference. The reference direction of blood vessel gradient may be defined commonly for all measurement locations of gradient, or may be defined individually for each measurement location. Alternatively, it is possible to divide all measurement locations into two or more groups and to define the reference direction individually for each group.

In OCT angiography, substantially the same area of eye fundus is iteratively scanned, and a blood vessel enhanced image is constructed based on a three dimensional data set including a plurality of two dimensional data sets acquired through the iterative scanning. The three dimensional data set constructed, for example, by scanning each of B cross sections (i.e., transverse sections) predetermined times (e.g., 4 times), constructing the predetermined number of images (i.e., B mode images) for each B cross section, and embedding the constructed B mode images in the same three dimensional coordinate system (and further, by voxelizing the embedded B mode images). Such image construction processing is known.

The ophthalmic imaging apparatus of the embodiment includes an optical system, a drive system, a control system, and a data processing system for performing OCT. The ophthalmic imaging apparatus of the embodiment is configured, for example, to be capable of performing Fourier domain OCT.

Fourier domain OCT includes spectral domain OCT and swept source OCT. Spectral domain OCT is an imaging technique that acquires the spectra of interference light in a space-divisional manner using a broadband, low coherence light source and a spectrometer, and construct an image of the subject's eye by applying Fourier transform on the spectra. Swept source OCT is an imaging technique that acquires the spectra of interference light in a time-divisional manner using a wavelength tunable light source (i.e., wavelength swept source) and an optical detector (e.g., balanced photo diode), and construct an image of the subject's eye by applying Fourier transform on the spectra. Applicable OCT technique is not limited to Fourier domain OCT; time domain OCT, enface OCT, or the like can be applied.

The ophthalmic imaging apparatus of the embodiment may include a modality (e.g., modality other than OCT) for obtaining images of the subject's eye and/or other sites. Typical examples of such modalities include a fundus camera (retinal camera), a scanning laser ophthalmoscope (SLO), a slit lamp microscope, and an ophthalmic operation microscope. The ophthalmic imaging apparatus of the embodiment may include a configuration for measuring characteristics of the subject's eye and/or other sites, a configuration for carrying out examinations, or the like.

The ophthalmic image processing apparatus of the embodiment includes the image processing function of the ophthalmic imaging apparatus. The OCT function of the ophthalmic imaging apparatus is not necessarily included in the ophthalmic image processing apparatus of the embodiment.

The data processing functions (e.g., calculation function, image processing function, control function, etc.) of the ophthalmic imaging apparatus and the ophthalmic image processing apparatus of the embodiment can be realized, for example, by the cooperation of hardware (e.g., a processor, a storage device, etc.) and software (e.g., a calculation program, an image processing program, a control program, etc.). Part of the hardware may be provided in an external apparatus that can communicate with the ophthalmic imaging apparatus (or the ophthalmic image processing apparatus). At least part of the software may be stored in the ophthalmic imaging apparatus (or the ophthalmic image processing apparatus) in advance, and/or, may be stored in an external apparatus that can communicate with the ophthalmic imaging apparatus (or the ophthalmic image processing apparatus) in advance.

<Ophthalmic Imaging Apparatus>
<Configuration>

Figure 1:
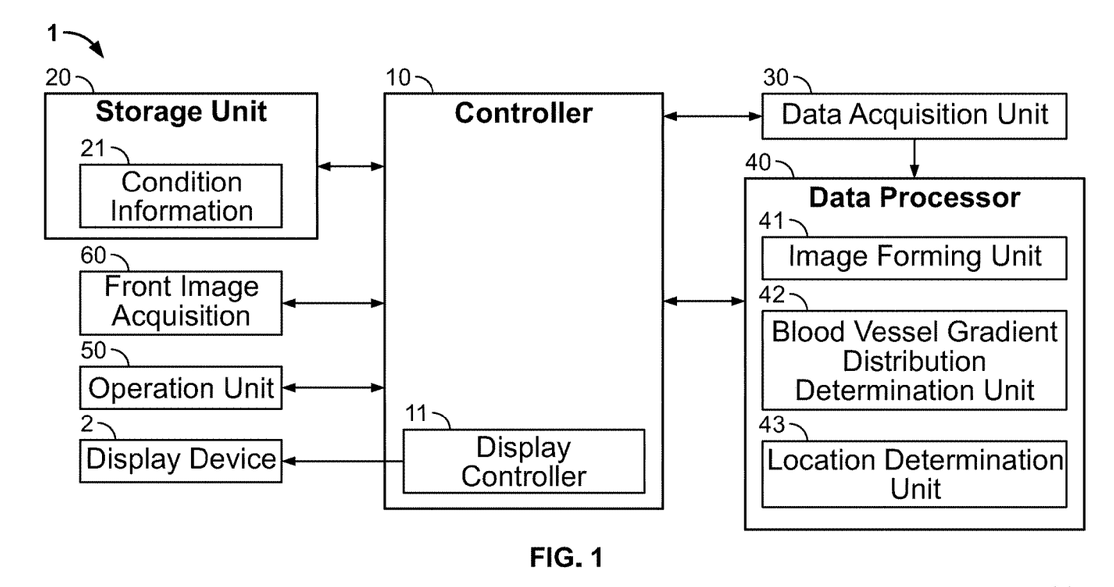
FIG. 1 is a schematic diagram illustrating the configuration of the exemplary ophthalmic imaging apparatus.

Exemplary embodiments of the ophthalmic imaging apparatus will be described. FIG. 1 shows an example of the configuration of the ophthalmic imaging apparatus. The ophthalmic imaging apparatus 1 acquires (or collects) a three dimensional data set of the fundus using OCT, forms a blood vessel enhanced image based on the three dimensional data set, and determines a blood vessel gradient distribution based on the blood vessel enhanced image. The ophthalmic imaging apparatus 1 can display the blood vessel gradient distribution and information obtained from the blood vessel gradient distribution on the display device 2. The display device 2 may be a part of the ophthalmic imaging apparatus 1, or may be configured as an external device connected to the ophthalmic imaging apparatus 1.

The ophthalmic imaging apparatus 1 includes the controller 10, the storage unit 20, the data acquisition unit 30, the data processor 40, the operation unit 50, and the front image acquisition unit 60.

<Controller 10>

The controller 10 controls each part of the ophthalmic imaging apparatus 1. The controller includes a processor(s). The processor includes a circuitry such as a central processing unit (CPU), a graphics processing unit (GPU), an application specific integrated circuit (ASIC), a programmable logic device (e.g., simple programmable logic device (SPLD), complex programmable logic device (CPLD)), a field programmable gate array (FPGA), or the like. The controller 10 is configured, for example, to read out and a computer program from a storage device or a storage circuit, and to execute the computer program, thereby performing a function according to the embodiment.

The controller 10 may include a communication device for transmitting and receiving data via a communication line such as a local area network (LAN), the internet, a private line, or the like.

<Display Controller 11>

The controller 10 includes the display controller 11. The display controller 11 executes control for displaying information on the display device 2. The display controller 11 can executes the display control based on information stored in the storage unit 20.

The display controller 11 executes processing (e.g., generation, process, manipulation, synthesis, etc.) related to information displayed on the display device 2. For instance, the display controller 11 can display the blood vessel gradient distribution (or information derived from the blood vessel gradient distribution) over an image acquired by the front image acquisition unit 60. The display controller 11 can synthesize an image acquired by the front image acquisition unit 60 and the blood vessel gradient distribution (or information derived from the blood vessel gradient distribution).

Such processing can be executed, for example, by the linkage of the display controller 11 and another element (e.g., another element in the controller 10, the data processor 40, etc.).

<Storage Unit 20>

The storage unit 20 stores various kinds of information. In the present embodiment, the condition information 21 is stored in advance. Note that the condition information 21 may be stored in an external device.

<Condition Information 21>

The condition information 21 includes one or more conditions related to gradients of blood vessels, and is referred to by the location determination unit 43. Some examples of the conditions included in the condition information 21 will be described.

The first example of the conditions is gradient range information for OCT blood flow measurement. Since OCT blood flow measurement treats Doppler OCT signals, suitable signals cannot be obtained unless the angle between the projection direction of the measurement light (i.e., A scan direction) and the blood flow direction is appropriate. It can be assumed that the blood flow direction is substantially the same as the orientation of the blood vessel at the projection position of the measurement light. Thus, it is important for OCT blood flow measurement to evaluate the gradient (i.e., inclination angle etc.) of the blood vessel against the A scan direction.

The gradient range information includes one or more conditions for evaluating blood vessel gradient against A scan direction. The conditions may include a threshold and/or range of blood vessel gradient. The gradient range information may include a condition related to subject's eyes, a condition related to the relationship between subject's eyes and the ophthalmic imaging apparatus 1. Examples of the condition related to subject's eyes include pupil diameter. Examples of the condition related to the relationship between subject's eyes and the ophthalmic imaging apparatus 1 include relative position between a subject's eye and the ophthalmic imaging apparatus 1 (e.g., deviation between the axis of a subject's eye and the optical system of the ophthalmic imaging apparatus 1).

Figure 2:
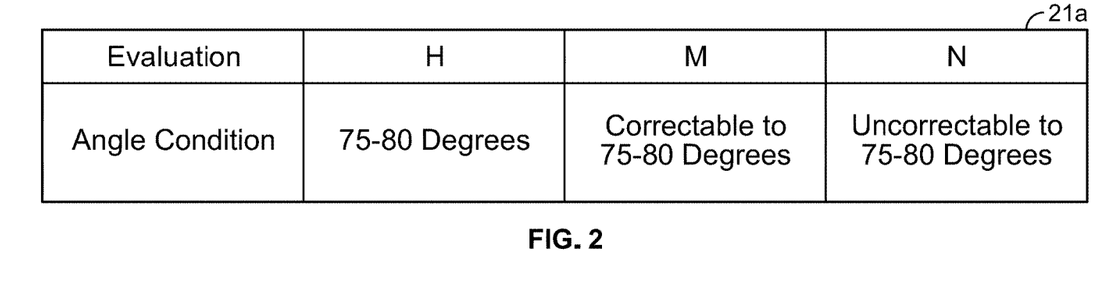
FIG. 2 is a schematic diagram illustrating the configuration of the exemplary ophthalmic imaging apparatus.

FIG. 2 shows an example of the gradient range information. The gradient range information 21a is included in the condition information 21. The gradient range information 21a is, for example, table information including the "EVALUATION" section and the "ANGLE CONDITION" section. The "EVALUATION" section shows evaluation ranks "H", "M", and "N". The "ANGLE CONDITION" section shows, as conditions related to blood vessel gradient, the angle condition "75-80 DEGREES" corresponding to the H rank, the angle condition "CORRECTABLE TO 75-80 DEGREES" corresponding to the M rank, and the angle condition "UNCORRECTABLE TO 75-80 DEGREES" corresponding to the N rank.

The evaluation ranks indicate the ranks of suitability for OCT blood flow measurement. For example, the H rank indicates the suitability "high", the M rank indicates the suitability "moderate", and the N rank indicates the suitability "none".

The angle condition corresponding to the H rank shows the blood vessel gradient (i.e., the angle of blood vessel against the A scan direction) highly suitable for OCT blood flow measurement. In the present embodiment, the angle range "75-80 DEGREES", which has been determined experimentally or clinically, can be assigned to the H rank.

The angle condition corresponding to the M rank shows the blood vessel gradient moderately suitable for OCT blood flow measurement. In the present embodiment, to the M rank, the condition that the suitable angle range "75-80 DEGREES" can be achieved through predetermined correction processing is assigned. The predetermined correction processing will be described later.

The angle condition corresponding to the N rank shows the blood vessel gradient unsuitable for OCT blood flow measurement. In the present embodiment, to the N rank, the condition that the suitable angle range "75-80 DEGREES" cannot be achieved even with the predetermined correction processing is assigned.

The correction processing used in the determination of the M rank and the N rank will be described. The correction processing includes the shift of the measurement light path from the axis of the subject's eye (i.e., the change of the relative position between the measurement light path and the axis of the subject's eye), for example. The amount of the shift is restricted by the pupil diameter. The pupil diameter may be a value obtained by measuring the subject's eye, or a standard value (e.g., statistic). The pupil diameter may be a pupil diameter value after mydriatic administration, or an estimated pupil diameter value under the influence of mydriatic administration.

In an exemplary correction processing, the location determination unit 43 determines whether or not the suitable angle range "75-80 DEGREES" is achieved when the measurement light path is shifted against the axis of the subject's eye using the pupil diameter as a constraint. The relationship between the shift of the measurement light path against the axis of the subject's eye and the projection direction (i.e., A scan direction) will be described. Note that, as described above, since the blood vessel gradient is defined using the A scan direction as a reference, the change in the A scan direction is equivalent to the change in the blood vessel gradient.

Figure 3:
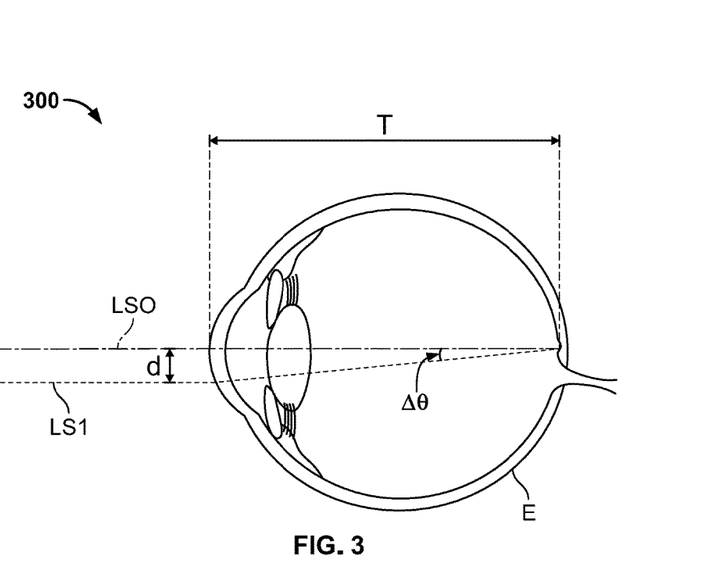
FIG. 3 is a schematic diagram for describing the processing executed by the exemplary ophthalmic imaging apparatus.

Now, FIG. 3 is referred to showing schematic diagram 300 for describing the processing executed by the exemplary ophthalmic imaging apparatus. The symbols LS0 and LS1 each shows the path of the measurement light (referred to as a measurement path). The measurement paths LS0 and LS1 are parallel to each other outside the subject's eye E and apart from each other by the distance d in the direction perpendicular to the measurement paths LS0 and LS1. That is, the measurement path LS1 is shifted from the measurement path LS0 by the distance d. The length of the measurement path LS0 inside the subject's eye E is denoted by T.

In such a case, the angle $\Delta\theta$ formed by the measurement path LS0 and the measurement path LS1 on the fundus can be calculated from the following formula: $\Delta\theta=\arctan(d/T)$. Further, the sign (+/−) of the angle $\Delta\theta$, that is, the sign (+/−) of the correction amount of the blood vessel gradient is determined according to the shift direction of the measurement path LS1 against the measurement path LS0. When the shift direction lies along the lengthwise direction of the blood vessel (more generally, when the vector indicating the shift includes a component in the lengthwise direction of the blood vessel, or when this component has a sufficiently large magnitude), the blood vessel gradient correction is carried out. On the other hand, when the shift direction does not lie along the lengthwise direction of the blood vessel (more generally, when the vector indicating the shift does not include a component in the lengthwise direction of the blood vessel, or when the magnitude of this component sufficiently small), the blood vessel gradient correction is not carried out.

The second example of the conditions will be described. The second example is local gradient distribution information for diagnosis of the subject's eye. Kinds of diseases to be diagnosed include diseases causing (characteristical) transformation of blood vessels. The local gradient distribution information includes a local distribution of blood vessel gradients corresponding to the characteristical blood vessel transformation. In a typical example, fundus blood vessels are bent in the cornea direction or the direction opposite thereto due to a tumor, body fluid leakage, or the like. Such a bending (or curve) is represented, for example, as a local distribution such that an interval in which the blood vessel gradient angle against the A scan direction gradually decreases and an interval in which the blood vessel gradient angle against the A scan direction gradually increases are arranged next to each other with the location corresponding to the blood vessel gradient angle 90 degrees between. The local gradient distribution information includes at least one such a characteristic local distribution.

The third example of the conditions will be described. The third example is chronological gradient variation information for diagnosis of the subject's eye. While the local gradient distribution information in the second example shows the shapes of blood vessels (at a certain time point), the chronological gradient variation information in the third example shows the chronological changes in the shapes of blood vessels. In a typical example, the transformation of blood vessels (e.g., the bending described above) advances along with the progression of the tumor, body fluid leakage, or the like. The change in the bending is represented, for example, as the change in the length of the interval in which the blood vessel gradient angle gradually decreases, the change in the length of the interval in which the blood vessel gradient angle gradually increases, the change in the height differences in the interval in which the blood vessel gradient angle gradually decreases, the change in the height differences in the interval in which the blood vessel gradient angle gradually increases, the change in the inclination in the interval in which the blood vessel gradient angle gradually decreases, the change in the inclination in the interval in which the blood vessel gradient angle gradually increases, or the like. The chronological gradient variation information includes at least one such a characteristic variation.

<Data Acquisition Unit 30>

The data acquisition unit 30 performs OCT on the subject's eye to acquire a three dimensional data set. The data acquisition unit 30 includes a configuration for performing measurements utilizing spectral domain OCT or swept source OCT, for example. The configuration includes, as in the convention, an optical system, a drive system, a data acquisition system (DAQ), a control system, and the like. The optical system includes an interference optical system, an optical scanner, and an optical detector. The interference optical system splits light output from a light source into measurement light and reference light, projects the measurement light onto the subject's eye, and superposes the return light of the measurement light from the subject's eye with the reference light to generate interference light. The optical scanner includes a Galvanometer scanner or the like and functions to deflect the measurement light. The optical detector detects (the spectra of) the interference light generated by the interference optical system.

The data acquisition unit 30 scans a three dimensional region of the subject's eye. The scan mode for this is, for example, raster scan (i.e., three dimensional scan). The raster scan is performed, for example, in such a manner that each of a plurality of B cross sections is scanned predetermined times (e.g., in such a manner that the B cross sections are scanned in a sequential order and each B cross section is scanned the predetermined times). The three dimensional data set acquired by the data acquisition unit 30 is sent to the data processor 40.

<Data Processor 40>

The data processor 40 executes various kinds of data processing. For example, the data processor 40 applies image processing and analysis processing on image data of the subject's eye. As a typical example, the data processor 40 executes rendering such as three dimensional computer graphics (3DCG) or the like. The data processor 40 includes the image forming unit 41, the blood vessel gradient distribution determination unit 42, and the location determination unit 43.

<Image Forming Unit 41>

The image forming unit 41 forms a plurality of cross sectional images (i.e., B mode images, or B scan images) for each of the B cross sections, based on the three dimensional data set acquired by the data acquisition unit 30. Such an image forming process includes noise elimination (noise reduction), filtering, fast Fourier transform (FFT), and the like as in the conventional OCT technique.

The image forming unit 41 may be configured to be capable of forming stack data by embedding the plurality of cross sectional images in a single three dimensional coordinate system. In the stack data, a predetermined number of cross sectional images are assigned to each B cross section. In addition, the image forming unit 41 may be configured to be capable of forming volume data (i.e., voxel data) by executing interpolation etc. on the stack data. In the volume data, a predetermined number of voxel groups are assigned to a position corresponding to each B cross section. The stack data and the volume data are examples of the three dimensional data set.

The image forming 41 can execute various kinds of rendering on the three dimensional data set to construct a B mode image (i.e., vertical cross sectional image, or cross sectional image along the axial direction), a C mode image (i.e., horizontal cross sectional image, or crosswise cross sectional image), a projection image, a shadowgram, and the like. An image of an arbitrary cross section, such as the B mode image and the C mode image, is constructed by selecting pixels (or voxels) on a designated cross section from the three dimensional data set. The projection image is constructed by projecting the three dimensional data set in a predetermined direction (e.g., Z direction, depth direction, or A scan direction). The shadowgram is constructed by projecting part of the three dimensional data set (e.g., partial data corresponding to a specific layer tissue) in a predetermined direction. An image of the subject's eye when viewed from its front side, such as the C mode image, the projection image, and the shadowgram, are referred to as a front image.

The image forming unit 41 may be configured to be capable of executing various kinds of image processing other than rendering. For instance, the image forming unit 41 can execute segmentation for determining a specific tissue or a specific tissue boundary, size analysis for determining the size (e.g., layer thickness, volume) of a specific tissue, or the like. When a specific layer tissue (or the specific layer tissue boundary) is determined through the segmentation, the image forming unit 41 can reconstruct a new B mode image or a new front image in which the specific layer tissue is transformed into a flat shape. Such an image is referred to as a flattened image.

The image forming unit 41 can form blood vessel enhanced image (i.e., angiogram). The angiogram is constructed by: specifying the image regions (blood vessel regions) corresponding to blood vessels through analyzing OCT data; and enhancing the specified blood vessel regions by changing the representation mode (or aspect) of the specified blood vessel regions. For the specification of blood vessel regions, a plurality of pieces of OCT data acquired through iteratively scanning substantially the same area of the subject's eye is used. In the present embodiment, the three dimensional data set is used for displaying an angiogram as a planar image.

The angiogram represents, for example, the distribution of blood vessels in a three dimensional region of the fundus that has been scanned using OCT. That is, the angiogram represents the three dimensional distribution of blood vessels. There are several kinds of methods for forming angiograms. A typical processing for angiogram formation will be described. In the processing to be described, a three dimensional data set is used. The three dimensional data set has been acquired through iteratively scanning each of a plurality of B cross sections of the subject's eye, and includes a plurality of B mode images arranged in chronological order for each of the B cross sections. Note that examples of the methods for iteratively scanning substantially the same B cross section include fixation and tracking.

The angiogram formation process begins with the position matching (or, registration, alignment, etc.) of the plurality of B mode images for each B cross section. The registration is executed, for example, using known image matching technique. In a typical example, the registration is achieved by extracting a feature region from each B mode image, and by executing position matching of the plurality of feature regions extracted from the plurality of B mode images to adjust the positions of the plurality of B mode images.

Next, changing image regions in the aligned B mode images are specified. The specification process includes, for example, a process of determining the difference between different B mode images. Each B mode image is an intensity image (or, luminance image, brightness image, etc.) that represents morphology of the subject's eye, and so it can be considered that image regions in the B mode image corresponding to tissues other than blood vessels are substantially changeless. On the other hand, since backscattering, which contributes to interference signals, changes randomly under the influence of blood flow, it can be inferred that image regions that change between the aligned B mode images are blood vessel regions. Such image regions correspond to, for example, pixels in which the values of the above difference are nonzero, or pixels in which the values of the above difference are greater than a predefined threshold.

To the image regions thus specified, information showing that the image regions correspond to blood vessels is given. By executing the above processing for the plurality of B cross sections, three dimensionally distributed blood vessel regions. By executing the rendering of a three dimensional blood vessel enhanced image constructed in this way, an image representing blood vessel distribution such as a front image, an image of an arbitrary cross section, or a shadowgram of an arbitrary area can be constructed.

The process of forming blood vessel enhanced images (i.e., angiograms) is not limited to the above. For example, conventional Doppler OCT technique or conventional image processing technique can be employed for the specification of blood vessel regions. In another example, by using different methods according to sites of the subject's eye, the specification of blood vessel regions can be executed for each site. For instance, while blood vessel regions of the retina are specified using the typical method described above or the Doppler OCT technique, blood vessel regions of the choroid are specified using the image processing method.

<Blood Vessel Gradient Distribution Determination Unit 42>

The blood vessel gradient distribution determination unit 42 determines a blood vessel gradient distribution based on the three dimensional angiogram formed by the image forming unit 41. The blood vessel gradient distribution shows gradients (or inclination angles) of blood vessels at a plurality of locations in the eye fundus. Examples of the determination of blood vessel gradients will be described. Note that the locations at which gradients are determined may be the plurality of A scan positions in the three dimensional data set, or may include a location between two adjacent A scan positions.

In the first example, the blood vessel gradient distribution determination unit 42 executes a thinning process on the blood vessel regions in the three dimensional angiogram to construct a blood vessel skeleton model. The thinning process can be performed with any known thinning algorithm.

The blood vessel gradient distribution determination unit 42 can be configured to calculate the gradient of the blood vessel skeleton model at an arbitrary location (location of interest, or interest location) to obtain the blood vessel gradient at the interest location. When the blood vessel skeleton model is differentiable at the interest location, the blood vessel gradient distribution determination unit 42 can calculate the gradient through differentiation. On the other hand, when the blood vessel skeleton model is not differentiable at the interest location, the blood vessel gradient distribution determination unit 42 can calculate (an approximate value of) the gradient at the interest location, for example, based on the position of the blood vessel skeleton at the interest location and the position(s) of the blood vessel skeleton at one or more neighborhood positions thereof.

Figure 4:
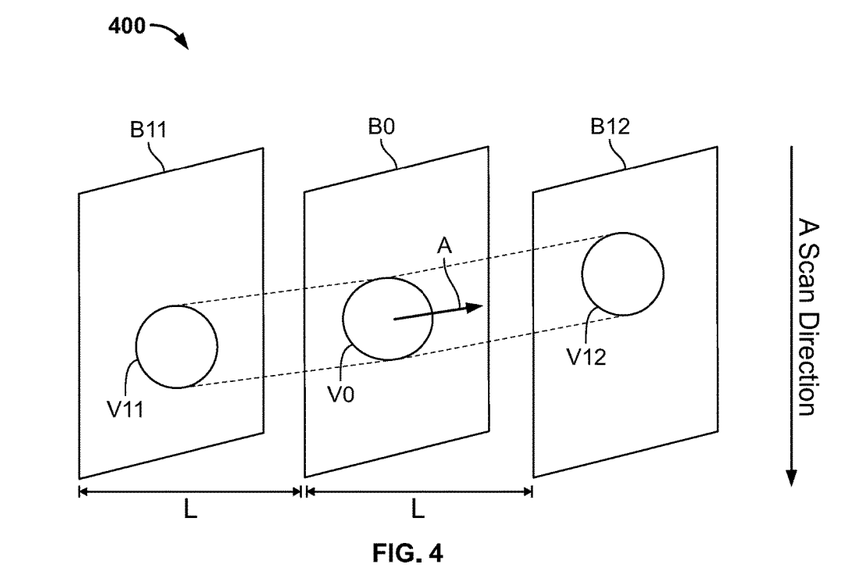
FIG. 4 is a schematic diagram for describing the processing executed by the exemplary ophthalmic imaging apparatus.

The second example will be described with referring to FIG. 4 showing schematic diagram 400 for describing the processing executed by the exemplary ophthalmic imaging apparatus. The symbol B0 indicates the cross sectional image representing the cross section including the interest location at which the blood vessel gradient is to be determined. Such a cross section is referred to as an interest cross section, and such cross sectional image is referred to as an interest cross sectional image. In the interest cross sectional image B0, the blood vessel region V0 is imaged. The symbols B11 and B12 indicate two cross sectional images representing two cross sections located near the interest cross sectional image B0. Such cross sections are referred to as neighbourhood cross sections, and such cross sectional images are referred to as neighbourhood cross sectional images. In the neighbourhood cross sectional image B11, the blood vessel region V11 that represents another cross section of the blood vessel identical with the blood vessel region V0 (that is, another cross section of the interest cross section) is imaged. Similarly, in the neighbourhood cross sectional image B12, the blood vessel region V12 that represents still another cross section of the interest cross section is imaged.

Here, for example, by applying a known process such as connected component labeling, region growing, or the like to the three dimensional angiogram, the locations (i.e., distribution) of the interest blood vessel can be determined and neighbourhood cross sections can be set. Note that it is possible to prepare a display function and a graphical user interface (GUI) can be prepared for the user to set at least one of the interest cross section and neighbourhood cross sections.

The blood vessel gradient distribution determination unit 42 calculates the gradient of the interest blood vessel at the interest cross section based on the interest cross sectional image B0 and the neighbourhood cross sectional images B11 and B12. Note that the number of neighbourhood cross sectional images referred to in this process is not limited to two, and may be arbitrary number equal to or more than one.

The blood vessel gradient distribution determination unit 42 calculates the gradient of the interest blood vessel at the interest cross section based on the blood vessel regions V0, V11, and V12, and a cross section interval. The cross section interval may include the distance between the neighbourhood cross sectional image B11 and the neighbourhood cross sectional image B12. Alternatively, the cross section interval may include at least one of the distance between the neighbourhood cross sectional image B11 and the interest cross sectional image B0 and the distance between the neighbourhood cross sectional image B12 and the interest cross sectional image B0. In the present example, the distance (i.e., interval) between the neighbourhood cross sectional image B11 (or B12) and the interest cross sectional image B0 is denoted by L.

The A scan direction shown in FIG. 4 (i.e., the direction indicated by the downward arrow) indicates, for example, the orientation of an A scan image(s) included in the interest cross sectional image B0 (e.g., the orientation of the A scan image arranged at the center among the plurality of A scan images included in the interest cross sectional image B0).

In one example, the blood vessel gradient distribution determination unit 42 can calculate the gradient A of the interest blood vessel at the interest cross section based on the positional relationship between three blood vessel regions V0, V11, and V12. The positional relationship can be obtained by connecting the blood vessel regions V0, V11, and V12 with a line(s). Specifically, the blood vessel gradient distribution determination unit 42 can specify a feature point in each of the three blood vessel regions V0, V11, and V12, and connects the specified feature points with a line. The feature point is, for example, the center, the center of gravity, the highest position, or the like. The line connecting the feature points is, for example, a line segment, an approximate curve (e.g., a spline curve, or a Bezier curve), or the like.

The blood vessel gradient distribution determination unit 42 calculates the gradient A based on the line(s) connecting the feature points. When a line segment(s) is used, the blood vessel gradient distribution determination unit 42 can calculate the gradient A, for example, based on the first line segment connecting the feature point in the blood vessel region V0 in the interest cross sectional image B0 and the feature point in the blood vessel region V11 in the neighbourhood cross sectional image B11, and based on the second line segment connecting the same feature point in the blood vessel region V0 and the feature point in the blood vessel region V12 in the neighbourhood cross sectional image B12. As an example of this calculation processing, the average value of the two line segments can be calculated. When connecting with an approximate curve, it is possible to calculate the gradient of the approximation curve at the intersection of the approximation curve and the interest cross section.

Blood vessel regions in three cross sections are taken into account in the present example; however, the gradient can be determined by taking blood vessel regions in two cross sections into account. As a specific example, the gradient A of the interest blood vessel at the interest cross section can be calculated based on the blood vessel region V11 in the neighborhood cross sectional image B11 and the blood vessel region V12 in the neighborhood cross sectional image B12. Alternatively, the gradient A of the interest blood vessel at the interest cross section can be calculated based on the blood vessel region V11 in the neighborhood cross sectional image B11 and the blood vessel region V0 in the interest cross sectional image B0. For example, the gradient of the first or second line segment described above can be determined, and the determined gradient can be set to be the gradient A of the interest blood vessel.

The above example determines a single value of the gradient A; however, two or more gradient values for two or more locations (or, two or more regions) in the blood vessel region V0 can be determined. In this case, the two or more gradient values determined can be used separately, or a single value (e.g., average value) obtained from the two or more gradient values through statistical calculation can be set to be the gradient A.

<Location Determination Unit 43>

The location determination unit 43 determines one or more locations in the eye fundus in which the gradients satisfy a predetermined condition based on the blood vessel gradient distribution obtained by the blood vessel gradient distribution determination unit 42. The predetermined condition is included in the condition information 21. The location determination unit 43, for example, executes the above-described processing on the condition information 21 to determine the one or more locations in the fundus.

When the predetermined condition includes the gradient range information (21a), the location determination unit 43 can determine, based on the blood vessel gradient distribution obtained by the blood vessel gradient distribution determination unit 42 and the gradient range information, whether one or more locations included in the blood vessel gradient distribution are suitable for OCT blood flow measurement. With this, for example, an evaluation rank(s) is assigned to at least part of the plurality of locations included in the blood vessel gradient distribution.

Here, at least one of the H rank, the M rank, and the N rank can be assigned, for example. Typically, locations corresponding to the H rank, locations corresponding to the M rank, and locations corresponding to the N rank can be determined. Alternatively, it may be configured to only assign locations corresponding to the H rank that are highly suitable for OCT blood flow measurement, to only assign locations corresponding to the M rank that are moderately suitable for OCT blood flow measurement, or to only assign locations corresponding to the N rank that are unsuitable for OCT blood flow measurement.

When the predetermined condition includes the local gradient distribution information, the location determination unit 43 can determine a site of a blood vessel in which characteristic deformation occurs (e.g., a site where the blood vessel has a characteristic shape) based on the blood vessel gradient distribution obtained by the blood vessel gradient distribution determination unit 42 and the local gradient distribution information. As described above, the characteristic deformation is, for example, the bending due to a tumor, body fluid leakage, or the like. In addition, the characteristic deformation can be detected as wandering of a blood vessel, local variation of blood vessel diameter, or the like.

When the predetermined condition includes the chronological gradient variation information, the location determination unit 43 can determine a site of a blood vessel in which characteristic chronological deformation occurs based on the blood vessel gradient distribution obtained by the blood vessel gradient distribution determination unit 42 and the chronological gradient variation information. As described above, the characteristic chronological deformation of blood vessel is caused by, for example, the progression of a tumor, body fluid leakage, or the like. In addition, the characteristic chronological deformation can be detected as chronological change in wandering of a blood vessel, chronological change in blood vessel diameter, or the like.

If the shift of the measurement path (see FIG. 3) intervenes in the case where the blood vessel gradient distribution is used for diagnosis, there is a risk that the accuracy of the comparison to the local gradient distribution information and the chronological gradient variation information is degraded owing to the change in the incident angle (projection angle) of the measurement light onto the fundus. For example, even when the same site in the fundus is to be measured, the apparent gradient angle of blood vessel changes depending on whether the measurement path is shifted or not, and therefore the result of comparison to the local gradient distribution information also changes. Similarly, when detecting the chronological change of blood vessel, it is difficult to say that comparing between a gradient angle obtained when the measurement path is shifted and a gradient angle obtained when the measurement path is not shifted is appropriate.

In view of such circumstances, it is possible, for example, to perform OCT blood flow measurement again according to the measurement path shift, to perform OCT blood flow measurement under the same shift state as in the past measurement, to correct the blood vessel gradient distribution based on shift amount, or the like. The correction of the blood vessel gradient distribution (which includes measurement values of gradient angles) according to shift amount can be executed, for example, in such a manner that the angle $\Delta\theta$ shown in FIG. 3 is to be canceled.

Note that the measurement path shift and/or its amount can be detected by employing a known configuration to perform position matching (i.e., alignment) between the optical system of the apparatus and the subject's eye. For example, the alignment state (e.g., the presence/absence of the shift, the amount of the shift) can be detected based on the position of a feature point (e.g., pupil center) in an anterior segment image acquired by anterior segment imaging of the subject's eye (using the front image acquisition unit 60). Alternatively, it is possible to project a light beam onto the cornea from an oblique direction, detect the reflection of the light beam, determine the corneal vertex position, and detect the alignment state from the corneal vertex position.

<Operation Unit 50>

The operation unit 50 is used for inputting instructions from the user to the ophthalmic imaging apparatus 1. The operation unit 50 may include known operation devices used in ophthalmic apparatuses, computers, or the like. For example, the operation unit 50 may include a mouse, a touch pad, a track ball, a keyboard, a pen tablet, an operation panel, a joy stick, a button, a switch, or the like. The operation unit 50 may include a touch panel. If this is the case, the controller 10 may be configured to display a GUI for the operation of the ophthalmic imaging apparatus 1 on the touch panel.

<Front Image Acquisition Unit 60>

The front image acquisition unit 60 acquires a front image of an eye fundus. Processes of front image acquisition are arbitrary. In the first example, the front image acquisition unit 60 can include a configuration for fundus imaging. An example of the front image acquisition unit 60 may include a fundus camera optical system, an SLO optical system, or the like.

In the second example, the front image acquisition unit 60 may include a configuration for obtaining a front image of the fundus of the subject's eye from an external apparatus. For example, the front image acquisition unit 60 may include a communication device for data transmission and reception through communication lines such as a LAN, the internet, a private line, or the like. If this is the case, the front image acquisition unit 60 can obtain a front image of the fundus of the subject's eye that is stored in a computerized medical records system, an image archiving system, or the like by using patient ID, DICOM tag, or the like as a search query.

In the third example, the front image acquisition unit 60 can form a front image using OCT. The OCT front image may be a C mode image, a projection image, a shadowgram, or the like.

When a front image is created through rendering of the three dimensional data set used for the angiogram formation, it is possible to perform registration between the angiogram and the front image via the common three dimensional data set (that is, via the common three dimensional coordinate system). In general, the registration between an angiogram and a front image can be performed, for example, through the process of detecting a feature site (e.g., optic nerve head, macula, blood vessel, lesion site, laser cicatrix) from the both images, and the process of matching the positions of the both images using the both feature sites as references.

<Operations>

Examples of the operation that can be carried out by an exemplary ophthalmic imaging apparatus will be described.

<First Operation Example>

Figure 5:
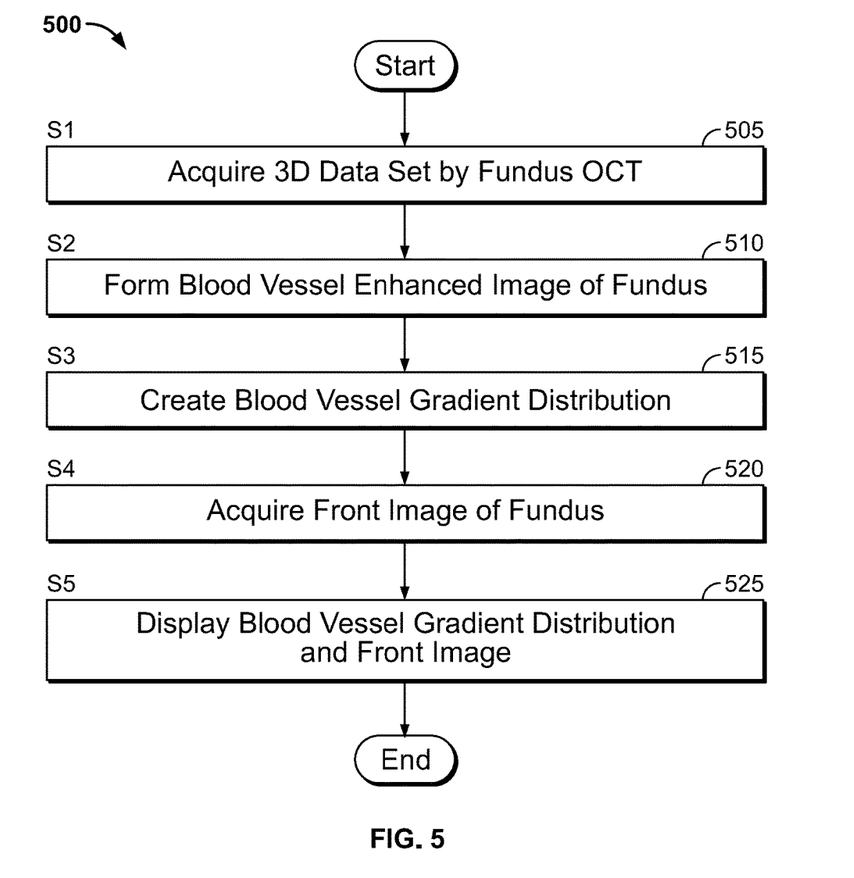
FIG. 5 is a flow chart of the operation of the exemplary ophthalmic imaging apparatus.

The first operation example displays the blood vessel gradient distribution of the fundus of the subject's eye together with the front image of the fundus. FIG. 5 shows flow chart 500 of the operations of the exemplary ophthalmic imaging apparatus describing processes executed in the present example. It is assumed that preparation processes have already been carried out (the same applies to other operations). The preparation processes include the alignment of the optical system with respect to the subject's eye, the focus adjustment of the optical system, the optical path length adjustment for OCT, the fixation position adjustment, OCT scan area setting, or the like.

(S1: Acquire Three Dimensional Data Set by Fundus OCT; Step 505 Also Referred to Herein as S1)

For OCT angiography, the data acquisition unit 30 acquires a three dimensional data set of the fundus of the subject's eye using OCT under the control of the controller 10. The acquired three dimensional data set is sent to the data processor 40.

(S2: Form Blood Vessel Enhanced Image of Fundus; Step 510 Also Referred to Herein as S2)

The image forming unit 41 forms a three dimensional enhanced image (three dimensional angiogram) based on the three dimensional data set acquired in the step S1.

(S3: Create Blood Vessel Gradient Distribution; Step 515 Also Referred to Herein as S3)

The blood vessel gradient distribution determination unit 42 determines a blood vessel gradient distribution showing blood vessel inclination angles at a plurality of locations in the fundus based on the three dimensional angiogram formed in the step S2. The blood vessel gradient distribution created is stored in the storage unit 20, for example.

(S4: Acquire Front Image of Fundus; Step 520 Also Referred to Herein as S4)

The front image acquisition unit 60 acquires a front image of the fundus, for example, by accessing the computerized medical records system or the like, imaging the fundus, or rendering the three dimensional data set acquired in the step S1.

The timing of carrying out the front image acquisition is arbitrary. For example, the front image acquisition can be performed by accessing the computerized medical records system or the like, or imaging the fundus before or after the step S1. Alternatively, the front image acquisition can be performed by rendering the three dimensional data set acquired in the step S1 at an arbitrary timing after the step S1.

(S5: Display Blood Flow Vessel Gradient Distribution and Front Image; Step 525 Also Referred to Herein as S5)

The display controller 11 controls the display device 2 to display the blood vessel gradient distribution created in the step S3 and the front image acquired in the step S4. Here, the display controller 11 or the data processor can execute the registration between the blood vessel gradient distribution and the front image.

In a typical example, the display controller 11 displays the blood vessel gradient distribution over the front image based on the result of the registration. In addition, the transmittance of the blood vessel gradient distribution can be adjusted by setting the alpha values of the blood vessel gradient distribution. With such a display mode, the user can easily understand the distribution of the blood vessel gradients in the fundus.

Display modes of the blood vessel gradient distribution will be described. The display controller 11 can assign pseudo colors according to blood vessel gradients to the blood vessel gradient distribution, for example. Further, the display controller 11 may be configured to selectively display only locations in which the gradient value belongs to a predefined range (e.g., the gradient value is greater than a predefined threshold, smaller than a predefined threshold, within a predefined range, outside a predefined range, or the like). The display controller 11 may be configured to display locations in which the gradient value belongs to the predefined range in a display mode different from that for other locations.

<Second Operation Example>

Figure 6:
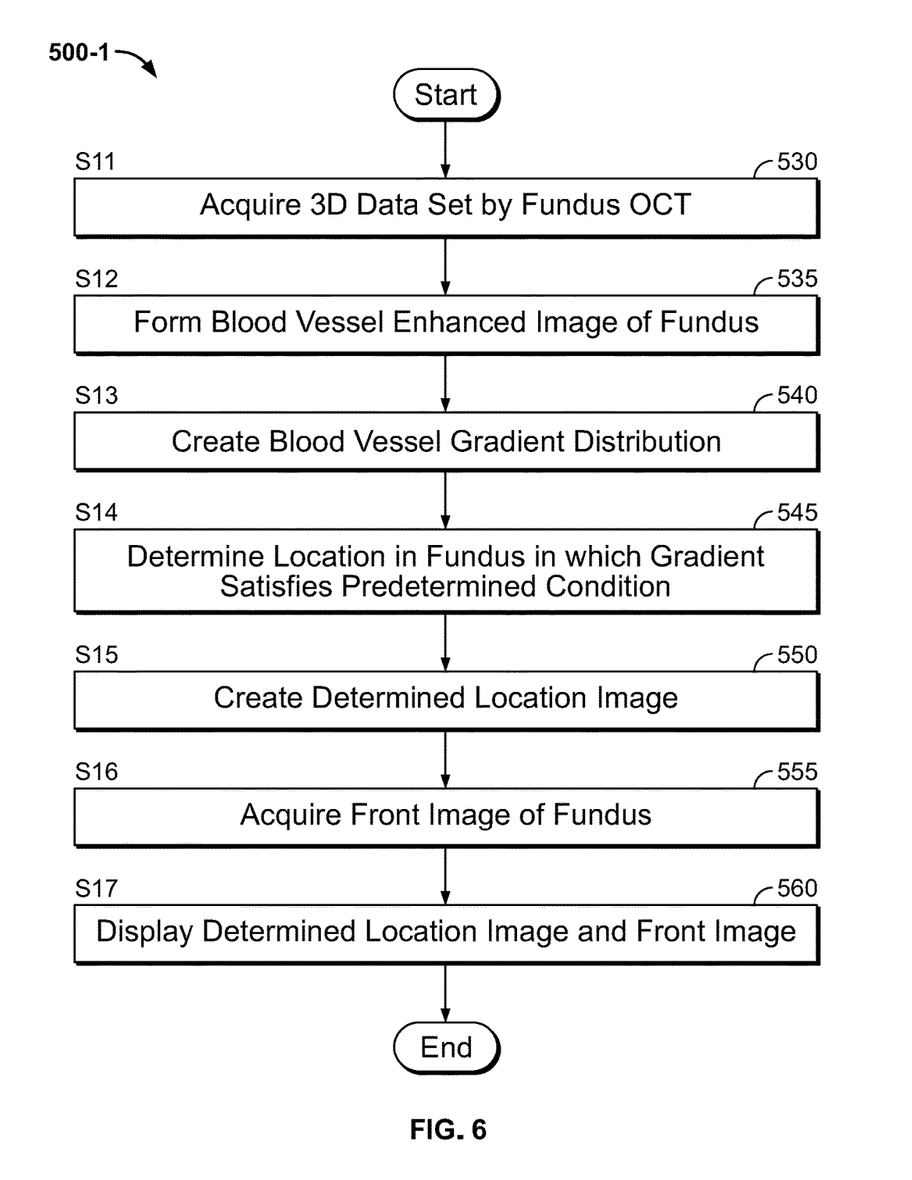
FIG. 6 is a flow chart of the operation of the exemplary ophthalmic imaging apparatus.

The second operation example displays, together with the front image of the fundus, locations in which blood vessel gradients satisfy the predefined condition. FIG. 6 shows flowchart 500-1 of processes executed in the present example.

(S11 to S13)

The steps S11 (Step 530 also referred to herein as S11), S12 (Step 535 also referred to herein as S12), and S13 (Step 540 also referred to herein as S13) are performed in the same manner as the steps S1, S2, and S3 of the first operation example, respectively.

(S14: Determine Location in Fundus in which Gradient Satisfies Predetermined Condition; Step 545 Also Referred to Herein as S14)

The location determination unit 43 determines one or more locations in the eye fundus in which the gradients satisfy the predetermined condition (e.g., condition information 21) based on the blood vessel gradient distribution created in the step S13.

(S15: Create Determined Location Image; Step 550 Also Referred to Herein as S15)

The data processor 40 and/or the display controller 11 create(s) an image(s) showing the one or more locations determined in the step S14. Such an image is referred to as a determined location image. The determined location image is, for example, an image formed by assigning pseudo colors to the locations determined in the step S14.

When considering a plurality of conditions, it is possible to assign different pseudo colors according to the conditions. For example, when the gradient range information 21a is shown in FIG. 2 is applied, "blue" is assigned to the locations classified as the H rank, "yellow" is assigned to the locations classified as the M rank, and "red" is assigned to the locations classified as the N rank.

When the local gradient distribution information is applied, for example, it is possible to assign pseudo colors to the locations where the blood vessel has a characteristic shape possibly caused by a tumor, body fluid leakage, or the like. Here, different pseudo colors can be assigned according to the degrees of lesions. For instance, "black" is assigned to the locations where the degrees of the lesions are thought to be severe, "red" is assigned to the locations where the degrees of the lesions are thought to be middle, "yellow" is assigned to the locations where the degrees of the lesions are thought to be low, and "blue" is assigned to the locations where the sites are thought to be normal. When the chronological gradient variation information is applied, a determined location image can be created in an analogous manner.

(S16: Acquire Front Image of Fundus; Step 555 Also Referred to Herein as S16)

The front image acquisition unit 60 acquires a front image of the fundus in the same manner as in the step S4 of the first operation example.

(S17: Display Determined Location Image and Front Image; Step 560 Also Referred to Herein as S17)

The display controller 11 controls the display device 2 to display the determined location image created in the step S15 and the front image acquired in the step S16. Here, the display controller 11 or the data processor 40 can executes the registration between the determined location image and the front image. The registration can be carried out, for example, via the three dimensional data set common to the determined location image and the front image, or through the feature site detection processing.

In a typical example, the display controller 11 displays the determined location image over the front image based on the result of the registration. In addition, the transmittance of the determined location image can be adjusted by setting the alpha values of the determined location image. With such a display mode, the user can easily understand the distribution of the locations in the fundus in which their blood vessel gradients satisfy the predefined condition.

<Third Operation Example>

Figure 7:
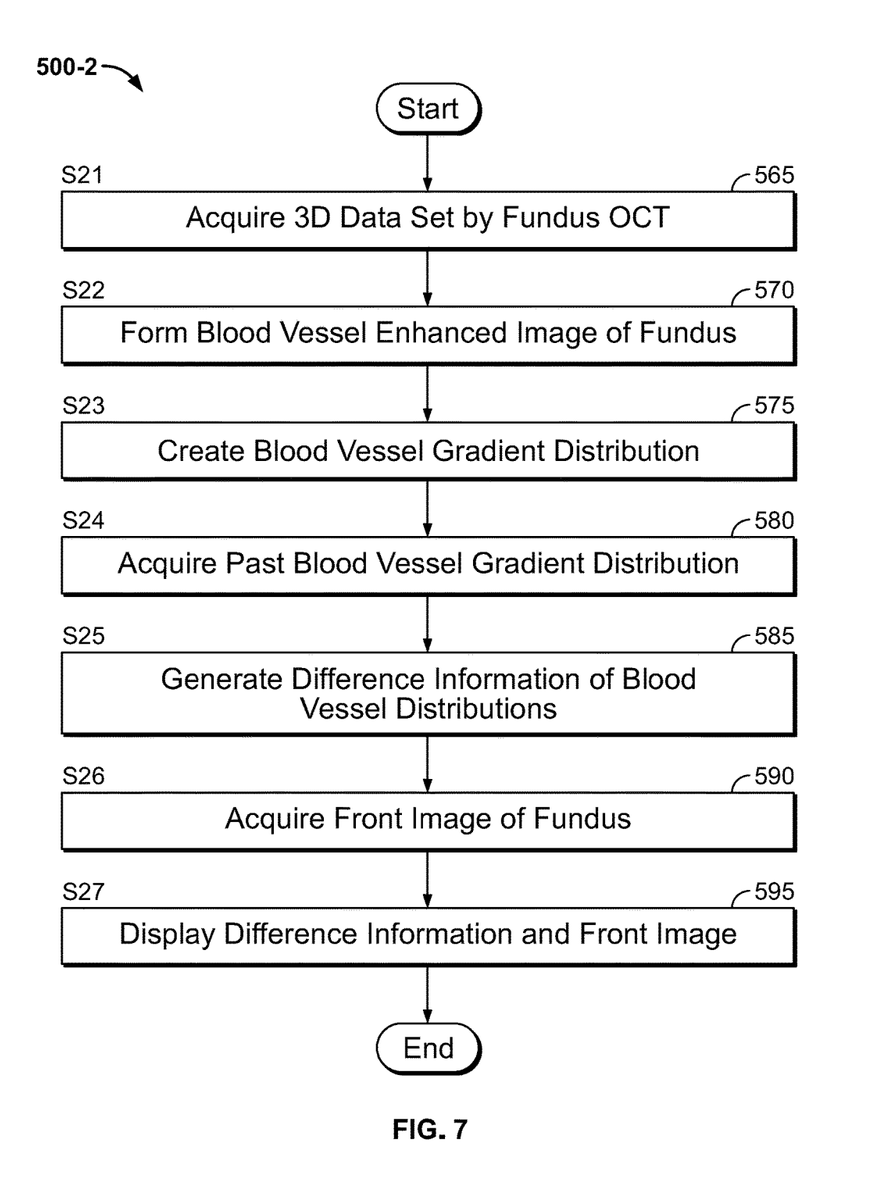
FIG. 7 is a flow chart of the operation of the exemplary ophthalmic imaging apparatus.

The third operation example displays an image showing the chronological change in blood vessel gradients together with the front image of the fundus. FIG. 7 shows flowchart 500-2 of processes executed in the present example.

(S21 to S23)

The steps S21 (Step 565 also referred to herein as S21), S22 (Step 570 also referred to herein as S22), and S23 (Step 575 also referred to herein as S1) are performed in the same manner as the steps S1, S2, and S3 of the first operation example, respectively.

(S24: Acquire Past Blood Vessel Gradient Distribution; Step 580 Also Referred to Herein as S24)

The controller 10 accesses an external apparatus via a communication line and acquires (one or more) blood vessel gradient distribution obtained in the past for the same subject's eye. Such a past blood vessel gradient distribution is, for example, stored in or associated with the electronic medical record of the subject.

(S25: Generate Difference Information of Blood Vessel Gradient Distributions; Step 585 Also Referred to Herein as S25)

The data processor 40 and/or the display controller 11 generate(s) difference information between the two or more blood vessel gradient distributions acquired in the steps S23 and S24. Here, the registration between the two or more blood vessel gradient distributions is executed by the use of the feature site detection processing.

The difference information is generated, for example, by calculating, for each location after the registration, the difference amount of the blood vessel gradient distribution newly acquired in the step S23 to the past blood vessel gradient distribution(s) acquired in the step S24. Examples of the types of the difference information include an image showing the distribution of the difference amounts in comparison with a predefined blood vessel gradient distribution (i.e., baseline distribution), a graph or a table in which predefined parameters (e.g., locations, times) and difference amounts are associated with each other, and a value calculated through statistical processing of a plurality of difference amounts. When the difference information is an image, pseudo colors can be assigned to the image under a predefined rule.

(S26: Acquire Front Image of Fundus; Step 590 Also Referred to Herein as S26)

The front image acquisition unit 60 acquires a front image of the fundus in the same manner as in the step S4 of the first operation example.

(S27: Display Difference Information and Front Image; Step 595 Also Referred to Herein as S27)

The display controller 11 controls the display device 2 to display the difference information generated in the step S25 and the front image acquired in the step S26. Here, the display controller 11 or the data processor 40 can executes the registration between the difference information and the front image.

In a typical example, the display controller 11 displays an image corresponding to the difference information (referred to as a difference image) over the front image based on the result of the registration. In addition, the transmittance of the difference image can be adjusted by setting the alpha values of the difference image. With such a display mode, the user can easily find the locations where the blood vessel gradients chronologically change.

In another example, the display controller 11 can display the graph, the table, or the value corresponding to the difference information and the front image side by side.

Note that while the present example generates the difference information showing the chronological change in blood vessel gradient distributions, difference information showing the chronological change in a parameter other than blood vessel gradient distributions can be generated and displayed together with a front image or the like. In a specific example, it is possible to generate difference information showing the chronological change of determined location images described in the second operation example.

<Fourth Operation Example>

Figure 8:
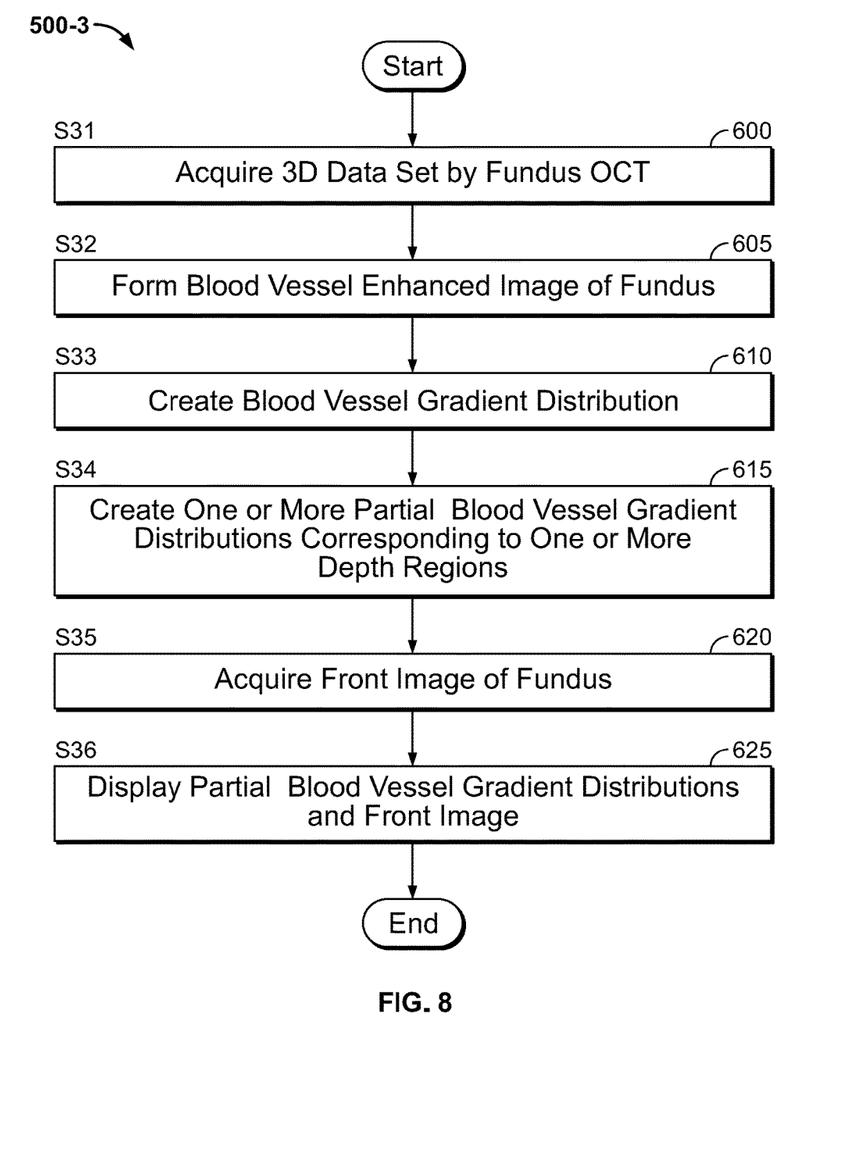
FIG. 8 is a flow chart of the operation of the exemplary ophthalmic imaging apparatus.

The fourth operation example displays blood vessel gradient distributions for different depth regions (referred to as partial blood vessel gradient distributions) together with the front image of the fundus. FIG. 8 shows flowchart 500-3 of processes executed in the present example.

(S31 to S33)

The steps S31 (Step 600 also referred to herein as S31), S32 (Step 605 also referred to herein as S32), and S33 (Step 610 also referred to herein as S33) are performed in the same manner as the steps S1, S2, and S3 of the first operation example, respectively.

(S34: Create One or More Partial Blood Vessel Gradient Distributions Corresponding to One or More Depth Regions; Step 615 Also Referred to Herein as S34)

The data processor 40 and/or the display controller 11 create(s) a partial blood vessel gradient distribution corresponding to each of one or more depth regions, based on the blood vessel gradient distribution created in the step S33 (or, based on the three dimensional angiogram acquired in the step S32).

Examples of the depth regions include the retina, one or more sub-tissues of the retina, the choroid, one or more sub-tissues of the choroid, the sclera, the vitreous body, the excavation of the optic nerve head, lamina cribrosa, and the like. The depth regions are set automatically or manually.

The blood vessel gradient distribution is generated from the three dimensional angiogram showing the three dimensional distribution of blood vessels. Hence, it is possible to generate the blood vessel gradient distribution in which three dimensional positions of blood vessels and the gradients of the blood vessels at the three dimensional positions are associated with each other. Segmentation of the blood vessel gradient distribution thus generated gives the partial blood vessel gradient distributions. The segmentation may be a segmentation process including the analysis of the three dimensional blood vessel gradient distribution. Alternatively, the partial blood vessel gradient distributions can be created by reflecting the result of the segmentation of the three dimensional data set acquired in the step S31 or an image formed from the three dimensional data set (e.g., ordinary OCT image, angiogram) to the three dimensional blood vessel gradient distribution. In addition, it is possible to execute the rendering of the partial blood vessel gradient distributions. For example, a shadowgram can be created based on a partial blood vessel gradient distribution.

(S35: Acquire Front Image of Fundus; Step 620 Also Referred to Herein as S35)

The front image acquisition unit 60 acquires a front image of the fundus in the same manner as in the step S4 of the first operation example. Here, a front image (shadowgram) can be created for each of one or more depth regions.

(S36: Display Partial Blood Vessel Gradient Distributions and Front Image; Step 625 Also Referred to Herein as S36)

The display controller 11 controls the display device 2 to display the partial blood vessel gradient distributions created in the step S34 and the front image acquired in the step S35. Here, the display controller 11 or the data processor 40 can executes the registration between the partial blood vessel gradient distributions and the front image.

In a typical example, the display controller 11 displays a partial blood vessel gradient distribution over the front image based on the result of the registration. In addition, the transmittance of the partial blood vessel gradient distribution can be adjusted by setting the alpha values of the partial blood vessel gradient distribution. With such a display mode, the user can easily understand the distributions of blood vessel gradients for the respective depth regions.

When two or more partial blood vessel gradient distributions corresponding to two or more depth regions are created, the partial blood vessel gradient distributions can be selectively displayed, or can be displayed side by side. Further, it is possible to display two or more partial blood vessel gradient distributions to which different pseudo colors are associated in a mutually overlapping manner.

Note that while the present example generates the partial blood vessel gradient distributions for the respective depth regions, another kind of partial information can be generated and displayed together with a front image or the like. In a specific example, it is possible to generate partial determined location images for the respective depth regions from the determined location image described in the second operation example.

<Actions and Effects>

Actions and effects of the exemplary ophthalmic imaging apparatuses will be described.

The ophthalmic imaging apparatus (1) of the embodiment includes a data acquisition unit (30), a blood vessel enhanced image forming unit (image forming unit 41), and a blood vessel gradient distribution determination unit (42). The data acquisition unit is configured to acquire a three dimensional data set of a fundus of a subject's eye using OCT. The blood vessel enhanced image forming unit is configured to form a blood vessel enhanced image based on the three dimensional data set. The blood vessel gradient distribution determination unit is configured to determine a blood vessel gradient distribution that shows gradients of blood vessels at a plurality of locations in the fundus, based on the blood vessel enhanced image.

In the embodiment, the blood vessel gradient distribution determination unit may be configured to determine an angle of a blood vessel against an A scan direction at each of the plurality of locations.

The ophthalmic imaging apparatus of the embodiment may further include a front image acquisition unit (60) configured to acquire a front image of the fundus, and a first display controller (display controller 11) configured to display the blood vessel gradient distribution and the front image on a display device (2).

The ophthalmic imaging apparatus of the embodiment may further include a location determination unit (43) configured to determine one or more locations in the fundus where gradients satisfy a predetermined condition (condition information 21, gradient range information 21*a*), based on the blood vessel gradient distribution.

The ophthalmic imaging apparatus of the embodiment may further include a front image acquisition unit (60) configured to acquire a front image of the fundus, and a second display controller (display controller 11) configured to display an image showing the one or more locations and the front image on a display device (2).

In the embodiment, the predetermined condition (condition information 21) may include gradient range information (21*a*) for performing OCT blood flow measurement. In addition, the location determination unit may be configured to determine the one or more locations based on the blood vessel gradient distribution and the gradient range information.

In the embodiment, the predetermined condition (condition information 21) may include local gradient distribution information for making a diagnosis. In addition, the location determination unit may be configured to determine the one or more locations based on the blood vessel gradient distribution and the local gradient distribution information.

In the embodiment, the predetermined condition (condition information 21) may include chronological gradient variation information for making a diagnosis. In addition, the location determination unit may be configured to determine the one or more locations based on two or more blood vessel gradient distributions of the fundus obtained on different dates and the chronological gradient variation information.

The ophthalmic imaging apparatus of the embodiment may further include a third display controller (display controller 11) configured to display the two or more blood vessel gradient distributions of the fundus obtained on different dates or difference information based on the two or more blood vessel gradient distributions on a display device (2).

The ophthalmic imaging apparatus of the embodiment may further include a fourth display controller (display controller 11) configured to display one or more partial blood vessel gradient distributions corresponding to one or more depth regions of the fundus on a display device (2), based on the blood vessel gradient distribution.

The embodiment thus configured can provide novel information showing the distribution of blood vessel gradients in the fundus (i.e., the blood vessel gradient distribution). The blood vessel gradient distribution may be used in the selection of blood vessels for performing OCT blood flow measurement, the detection of lesions, diagnoses, or the like. However, the purposes of use of the blood vessel gradient distribution are not limited to them.

The actions and effects of the embodiment are not limited to the above, and actions and effects provided by each item described in the embodiment and actions and effects provided by any combination of a plurality of items should be taken into account.

<Ophthalmic Image Processing Apparatus>

Figure 9:
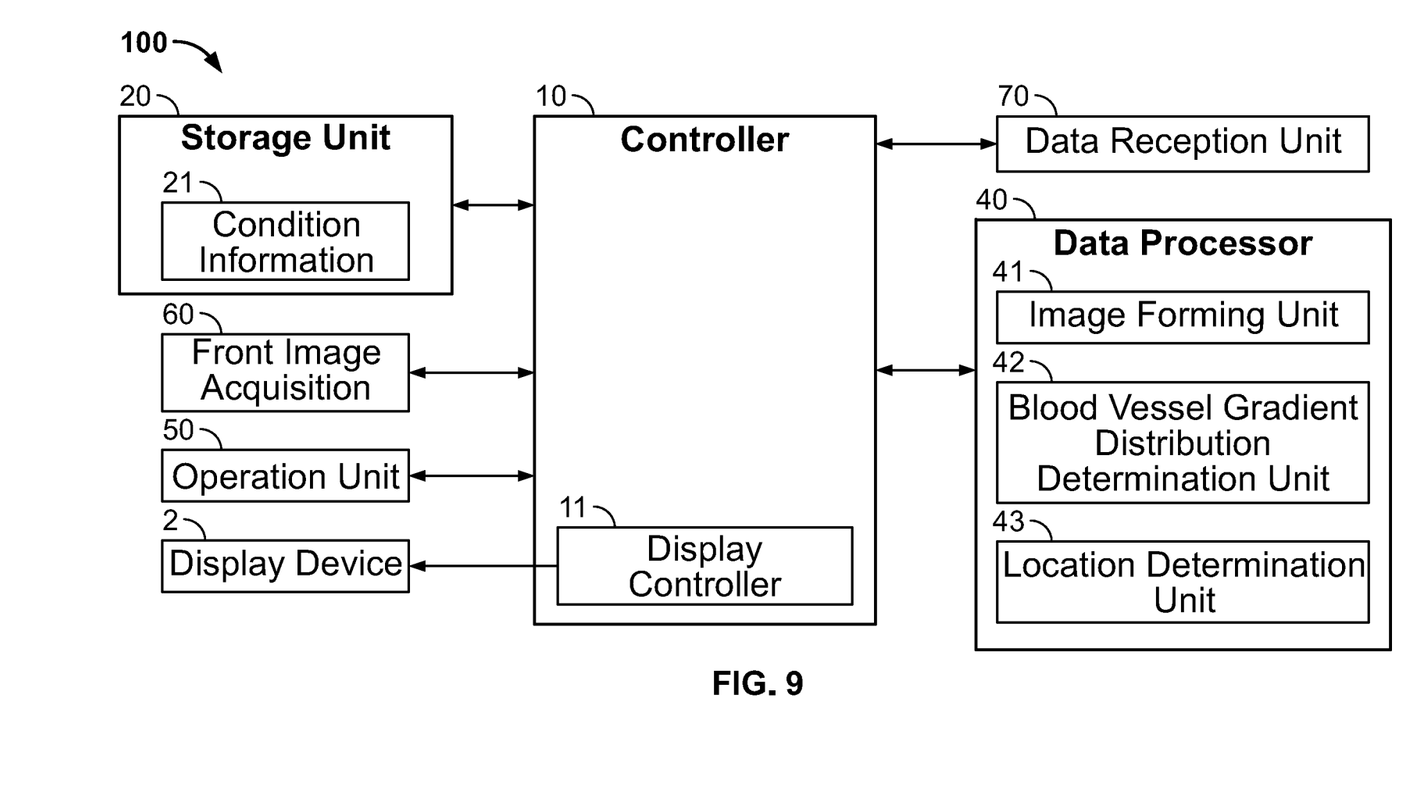
FIG. 9 is a schematic diagram illustrating the configuration of the exemplary ophthalmic image processing apparatus.

An exemplary ophthalmic image processing apparatus may include, for example, part of or whole the ophthalmic imaging apparatus according to the above embodiment. FIG. 9 shows the configuration of an exemplary ophthalmic image processing apparatus. Note that the same elements as those of the ophthalmic imaging apparatus according to the above embodiment 1 (see FIG. 1) are shown by the same symbols, and their descriptions are omitted unless otherwise stated.

The ophthalmic image processing apparatus 100 includes the controller 10, the storage 20, the data processor 40, operation unit 50, and the front image acquisition unit 60, each of which is configured in the same manner as in the ophthalmic imaging apparatus 1. Each of these elements has at least part of the functions of the corresponding element described in the above embodiment. In addition, the ophthalmic image processing apparatus 100 includes the data reception unit 70. The ophthalmic image processing apparatus 100 does not need to include the data acquisition unit 30.

The data reception unit 70 is configured to receive a three dimensional data set of the fundus of the subject's eye acquired using optical coherence tomography (OCT). The data reception unit 70 may include a communication device for transmitting and receiving data via a communication line such as a LAN, the internet, a private line, or the like. The data reception unit 70 may include a data reader for reading out data from a recording medium.

The image forming unit 41 (blood vessel enhanced image forming unit) is configured to form a blood vessel enhanced image based on the three dimensional data set. received by the data reception unit 70. The blood vessel gradient distribution determination unit is configured to determine a blood vessel gradient distribution that shows gradients of blood vessels at a plurality of locations in the fundus, based on the blood vessel enhanced image.

In addition, the ophthalmic image processing apparatus 100 may be configured to execute part of or all the processes executable by the ophthalmic imaging apparatus 1 (see the above embodiment).

According to the ophthalmic image processing apparatus 100 thus configured can provide, as the ophthalmic imaging apparatus 1, novel information showing the distribution of blood vessel gradients in the fundus (i.e., the blood vessel gradient distribution). The blood vessel gradient distribution may be used in the selection of blood vessels for performing OCT blood flow measurement, the detection of lesions, diagnoses, or the like. However, the purposes of use of the blood vessel gradient distribution are not limited to them.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic imaging apparatus comprising:
   an optical coherence tomography (OCT) data acquisition unit configured to acquire a three dimensional data set of a fundus of a subject's eye; and
   a processor comprising:
      a blood vessel enhanced image forming unit configured to form a blood vessel enhanced image based on the three dimensional data set;
      a blood vessel gradient distribution determination unit configured to determine a blood vessel gradient distribution that shows gradients of blood vessels at a plurality of locations in the fundus, based on the blood vessel enhanced image; and
      a location determination unit configured to determine one or more locations in the fundus where gradients satisfy a predetermined condition, based on the blood vessel gradient distribution,
   wherein the predetermined condition includes chronological gradient variation information for making a diagnosis, and the location determination unit determines the one or more locations based on two or more blood vessel gradient distributions of the fundus obtained on different dates and the chronological gradient variation information.

2. The ophthalmic imaging apparatus of claim 1, wherein the blood vessel gradient distribution determination unit determines an angle of a blood vessel against an axial scan direction at each of the plurality of locations.

3. The ophthalmic imaging apparatus of claim 1, further comprising:
a front image acquisition unit configured to acquire a front image of the fundus; and
a first display controller configured to display the blood vessel gradient distribution and the front image on a display device.

4. The ophthalmic imaging apparatus of claim 1, further comprising:
a front image acquisition unit configured to acquire a front image of the fundus; and
a second display controller configured to display an image showing the one or more locations and the front image on a display device.

5. The ophthalmic imaging apparatus of claim 1, wherein the predetermined condition includes gradient range information for performing OCT blood flow measurement, and
the location determination unit determines the one or more locations based on the blood vessel gradient distribution and the gradient range information.

6. The ophthalmic imaging apparatus of claim 1, wherein the predetermined condition includes local gradient distribution information for making a diagnosis, and
the location determination unit determines the one or more locations based on the blood vessel gradient distribution and the local gradient distribution information.

7. The ophthalmic imaging apparatus of claim 1, further comprising a third display controller configured to display the two or more blood vessel gradient distributions of the fundus obtained on different dates or difference information based on the two or more blood vessel gradient distributions on a display device.

8. The ophthalmic imaging apparatus of claim 1, further comprising a fourth display controller configured to display one or more partial blood vessel gradient distributions corresponding to one or more depth regions of the fundus on a display device, based on the blood vessel gradient distribution.

9. An ophthalmic image processing apparatus comprising:
a receiver configured to receive a three dimensional data set of a fundus of a subject's eye acquired using optical coherence tomography (OCT); and
a processor comprising:
a blood vessel enhanced image forming unit configured to form a blood vessel enhanced image based on the three dimensional data set;
a blood vessel gradient distribution determination unit configured to determine a blood vessel gradient distribution that shows gradients of blood vessels at a plurality of locations in the fundus, based on the blood vessel enhanced image; and
a location determination unit configured to determine one or more locations in the fundus where gradients satisfy a predetermined condition, based on the blood vessel gradient distribution,
wherein
the predetermined condition includes chronological gradient variation information for making a diagnosis, and
the location determination unit determines the one or more locations based on two or more blood vessel gradient distributions of the fundus obtained on different dates and the chronological gradient variation information.

* * * * *